(12) United States Patent
Militzer et al.

(10) Patent No.: US 8,034,961 B2
(45) Date of Patent: *Oct. 11, 2011

(54) PROCESS FOR STEREOSELECTIVELY REDUCING 4-ARYL-4-OXOBUTANOIC ACID DERIVATIVES

(75) Inventors: Hans-Christian Militzer, Odenthal (DE); Boris Bosch, Köln (DE); Markus Eckert, Shanghai (CN); Benjamin Meseguer, Tarragona (ES)

(73) Assignee: LANXESS Deutschland GmbH, Leverkusen, DE (US)

( * ) Notice: Subject to any disclaimer, the term of this patent is extended or adjusted under 35 U.S.C. 154(b) by 662 days.

This patent is subject to a terminal disclaimer.

(21) Appl. No.: 12/002,407

(22) Filed: Dec. 17, 2007

(65) Prior Publication Data

US 2008/0103316 A1 May 1, 2008

Related U.S. Application Data

(62) Division of application No. 11/153,053, filed on Jun. 15, 2005, now Pat. No. 7,329,766, which is a division of application No. 10/457,685, filed on Jun. 9, 2003, now Pat. No. 6,921,822.

(30) Foreign Application Priority Data

Jun. 7, 2002  (DE) ................................. 102 25 352

(51) Int. Cl.
| | | |
|---|---|---|
| C07D 333/12 | (2006.01) |
| C07D 333/20 | (2006.01) |
| C07C 233/00 | (2006.01) |
| C07C 235/00 | (2006.01) |
| C07C 237/00 | (2006.01) |
| C07C 239/00 | (2006.01) |
| C07C 211/00 | (2006.01) |

(52) U.S. Cl. .......................... 549/74; 564/123; 564/336
(58) Field of Classification Search ........................ None
See application file for complete search history.

(56) References Cited

U.S. PATENT DOCUMENTS 5,886,181 A    3/1999   Fuchs et al. ................... 544/388

FOREIGN PATENT DOCUMENTS

JP   9157196    6/1997
JP   2000143589  5/2000

OTHER PUBLICATIONS

Genet, et. al.; Tetrahedron letters, 36(27) pp. 4801-4804.*
Noyori, et. al., Acc. Chem. Res. 1977, 30, 97-102.*
Ramachandran, P., et al.; "Efficient Intramolecular Asymmetric Reductions . . . "; Org. Lett., 2001, vol. 3, No. 1, pp. 17-18.
Zassinovich et al. Chem Rev. 1992, 92,1051-1069.
March, J., Advanced Organic Chemistry 4th ED John Wiley and Sons, 1992, p. 541.
Wills et al. Tetrahedron Asymmetry 1999, 2045.
Noyari et al. JACS 1996, 118, 2521-2522.
Supporting Information for Above: Noyori et al. Acc Chem Res. 1997, 30,97-102.

* cited by examiner

*Primary Examiner* — Jeffrey Murray
(74) *Attorney, Agent, or Firm* — Michael A. Miller

(57) ABSTRACT

The present invention relates to a process for preparing stereoisomerically enriched 4-aryl-4-hydroxybutanoic acid derivatives by reducing 4-aryl-4-ketobutanoic acid derivatives in the presence of ruthenium-containing catalysts.

1 Claim, No Drawings

PROCESS FOR STEREOSELECTIVELY REDUCING 4-ARYL-4-OXOBUTANOIC ACID DERIVATIVES

This application is a Divisional of U.S. patent application Ser. No. 11/153,053 filed Jun. 15, 2005 now U.S. Pat. No. 7,329,766, entitled Process for Stereoselectively Reducing 4-Aryl-4-Oxobutanoic Acid Derivatives which was a Divisional of Ser. No. 10/457,685 filed Jun. 9, 2003 now U.S. Pat. No. 6,921,822, entitled Process for Stereoselectively Reducing 4-Aryl-4-Oxobutanoic Acid Derivatives, the contents of which are hereby incorporated by reference in their entirety.

BACKGROUND OF THE INVENTION

1. Field of the Invention

The present invention relates to a process for preparing stereoisomerically enriched 4-aryl-4-hydroxybutanoic acid derivatives by reducing 4-aryl-4-ketobutanoic acid derivatives in the presence of ruthenium-containing catalysts.

2. Brief Description of the Prior Art

Stereoisomerically enriched hydroxybutanoic acid derivatives are valuable intermediates, for example, in the preparation of liquid-crystalline compounds, agrochemicals and pharmaceuticals.

The catalytic reduction of ketones to stereoisomerically enriched secondary alcohols is known in principle. Useful reducing agents are customarily molecular hydrogen or, in the case of transfer hydrogenations, organic hydrogen donors, for example formic acid or isopropanol.

In EP A 744 401, Noyori et al. describe the enantioselective hydrogen hydrogenation of γ-keto esters and subsequent cyclization to the corresponding butyrolactones in the presence of chiral ruthenium complexes. A disadvantage is the extremely long reaction times of several days.

An advantage of transfer hydrogenations is that the safety measures which have to be taken when handling highly explosive molecular hydrogen under pressure are not required. In general, it is also possible to work at ambient pressure.

A review of transfer hydrogenations as a method for catalytically reducing ketones is given, for example, by Zassinovich et al. in Chem. Rev. 1992, 92, 1051-1069 and Noyori et al. in Acc. Chem. Res. 1997, 30, 97-102 and also Wills et al. in Tetrahedron, Asymmetry, 1999, 2045.

Noyori et al. (JACS 1996, 118, 2521-2522, Acc. Chem. Res. 1997, 30, 97-102) describe the use of ruthenium complexes as catalysts and triethylamine/formic acid as a hydrogen donor mixture for the enantioselective reduction of simple ketones.

However, there was also a need to provide an efficient process which allows the preparation of stereoisomerically enriched ▢aryl▢hydroxybutanoic acid derivatives from ▢aryl▢oxobutanoic acid derivatives.

SUMMARY OF THE INVENTION

A process has now been found for preparing stereoisomerically enriched 4-aryl-4-hydroxybutanoic acid derivatives which is characterized in that
a) compounds of the formula (I)

$$Ar-CO-CH_2CH_2W \qquad (I),$$

where

Ar is a mono-, bi or tricyclic aromatic radical having a total of 5 to 18 ring atoms, each cycle containing no, one, two or three ring atoms selected from the group of oxygen, sulphur and nitrogen, and the mono-, bi- or tricyclic aromatic radical being optionally mono or polysubstituted and W is $C(O)YR^1{}_n$ where Y is oxygen and n=1 or Y is nitrogen and n=2, or w is CN and $R^1$ is in each case independently hydrogen, $C_1$-$C_{20}$-alkyl, $C_4$-$C_{14}$-aryl or $C_5$-$C_{15}$-arylalkyl or, in the case that Y is nitrogen, both $R^1$ radicals together are $C_3$-$C_{12}$-alkylene, b) in the presence of a ruthenium-containing catalyst and
c) in the presence of at least one amine which is present at least partly in protonated form,
d) are reacted with formic acid, formates or mixtures thereof,
e) optionally in the presence of organic solvent.

DETAILED DESCRIPTION OF THE INVENTION

It is pointed out that the scope of the invention also encompasses any desired combination of the areas and areas of preference mentioned for each feature (e.g. parameter or structural feature).

Compounds of the formula (I) are obtainable, for example, in one step in a manner known in principle by Friedel-Crafts acylation from the corresponding aromatic and succinic anhydride in the presence of a Lewis acid such as aluminium chloride or tin chloride (see also J. March in Advanced Organic Chemistry, 4th Ed., John Wiley and Sons, 1992, page 541).

For the purposes of the invention, stereoisomerically enriched (enantiomerically enriched, diastereomerically enriched) 4-aryl-4-hydroxybutanoic acid derivatives are stereoisomerically pure (enantiomerically pure or diastereomerically pure) 4-aryl-4-hydroxybutanoic acid derivatives or mixtures of stereoisomeric (enantiomeric or diastereomeric) 4-aryl-4-hydroxybutanoic acid derivatives in which one stereoisomer (enantiomer or diastereomer) is present in a larger absolute proportion, preferably 70 to 100 mol % and very particularly preferably 85 to 100 mol %, than another diastereomer, or than the other enantiomer.

For the purposes of the invention, alkyl is, in each case independently, a straight-chain or cyclic, and, independently thereof, branched or unbranched, alkyl radical which may be further substituted by $C_1$-$C_4$-alkoxy radicals. The same applies for the alkyl moiety of an arylalkyl radical.

For the purposes of the invention, $C_1$-$C_4$-alkyl is, for example, methyl, ethyl, 2-ethoxyethyl, n-propyl, isopropyl, n-butyl and tert-butyl, $C_1$-$C_8$-alkyl is additionally, for example, n-pentyl, cyclohexyl, n-hexyl, n-heptyl, n-octyl or isooctyl, $C_1$-$C_{12}$-alkyl is further additionally, for example, norbornyl, n-decyl and n-dodecyl, and $C_1$-$C_{20}$ is still further additionally n-hexadecyl and n-octadecyl.

For the purposes of the invention, aryl is, for example and with preference, carbocyclic aromatic radicals or heteroaromatic radicals which contain no, one, two or three heteroatoms per cycle, but at least one heteroatom in the entire heteroaromatic radical which [lacuna] is selected from the group of nitrogen, sulphur and oxygen.

The carbocyclic aromatic radicals or heteroaromatic radicals may further be substituted by up to five substituents per cycle, each of which is, for example and with preference, independently selected from the group of hydroxyl, $C_1$-$C_{12}$-alkyl, cyano, COOH, COOM where M is an alkali metal ion or half an equivalent of an alkaline earth metal ion, COO—($C_1$-$C_{12}$-alkyl), COO—($C_4$-$C_{10}$-aryl), CO—($C_1$-$C_{12}$-alkyl), CO—($C_4$-$C_{10}$-aryl), O—($C_1$-$C_{12}$-alkyl), O—($C_4$-$C_{10}$-aryl), N($C_1$-$C_{12}$-alkyl)$_2$, NH—($C_1$-$C_{12}$-alkyl), fluorine, chlorine, bromine, $C_1$-$C_{12}$-fluoroalkyl where fluoroalkyl is a singly, multiply or fully fluorine-substituted alkyl radical as defined above, $CONH_2$, $CONH-(C_1-C_{12}$-alkyl), $NHCOO-(C_1-C_{12}$-alkyl). The same applies to the aryl moiety of an arylalkyl radical.

In formula (I), Ar is preferably a mono- or bicyclic aromatic radical having a total of 5 to 12 ring atoms, each cycle containing no, one or two ring atoms selected from the group of oxygen, sulphur and nitrogen, and the mono- or bicyclic aromatic radical bearing no, one, two or three radicals per cycle which are each independently selected from the group of hydroxyl, $C_1-C_{12}$-alkyl, cyano, COOH, COOM, COO—($C_1-C_{12}$-alkyl), COO—($C_4-C_{10}$-aryl), CO—($C_1-C_{12}$-alkyl), CO—($C_4-C_{10}$-aryl), O—($C_1-C_{12}$-alkyl), ($C_1-C_{12}$-alkyl)-O—($C_1-C_{12}$-alkyl), ($C_4-C_{10}$-aryl)-O—($C_1-C_{12}$-alkyl), O—($C_4-C_{10}$-aryl), O—CO—($C_4-C_{10}$-aryl), O—CO—($C_1-C_{12}$-alkyl), OCOO—($C_1-C_{12}$-alkyl), N—($C_1-C_{12}$-alkyl)$_2$, NH—($C_1-C_{12}$-alkyl), N($C_4-C_{10}$-aryl)$_2$, NH—($C_4-C_{10}$-aryl), fluorine, chlorine, bromine, iodine, $NO_2$, $SO_3H$, $SO_3M$, $SO_2$($C_1-C_{12}$-alkyl), SO($C_1-C_{12}$-alkyl), $C_1-C_{12}$-fluoroalkyl where fluoroalkyl is a singly, multiply or fully fluorine-substituted alkyl radical as defined above, NHCO—($C_1-C_{12}$-alkyl), $CONH_2$, CONH—($C_1-C_{12}$-alkyl), NHCOO—($C_1-C_{12}$-alkyl), PO($C_4-C_{10}$-aryl)$_2$, PO($C_1-C_{12}$-alkyl)$_2$, $PO_3H_2$, $PO_3M_2$, $PO_3HM$, PO(O($C_1-C_{12}$-alkyl)$_2$, where M is in each case an alkali metal ion or half an equivalent of an alkaline earth metal ion.

In formula (I), Ar is preferably phenyl, 1- or 2-naphthyl, 1-, 2-, 3- or 4-fluorenyl and 1-, 2- or 5-anthracenyl, phenanthrenyl, heteroaryl is particularly preferably 2- or 3-thiophenyl, 2- or 3-furanyl, 2- or 3-pyrrolyl, 3- or 4-pyrazolyl, 1-, 2-, or 4-thiazolyl, 1-, 2-, or 4-oxazolyl, 2-, 4- or 5-imidazolyl, 2-, 3-, or 4-pyridyl, 2- or 3-pyrazinyl, 2-, 4-, or 5-pyrimidyl, 3-, 4-, 5- or 6-pyridazinyl, 2- or 3-indolyl, 3-indazolyl, indazolyl, 2- or 3-benzofuranyl, 2- or 3-benzothiophen-yl, 2-, 3- or 4-quinolinyl, isoquinolinyl 2-, 4-, 6- or 7-pteridinyl or 2-, 3-, 4-, 5-, 6-, 8-, 9- or 10-phenanthrenyl where each of the radicals mentioned bears no, one or two radicals per cycle, each of which is independently selected from the group of $C_1-C_4$-alkyl, cyano, COO—($C_1-C_4$-alkyl), O—($C_1-C_4$-alkyl), N($C_1-C_4$-alkyl)$_2$, NH—($C_1-C_4$-alkyl), fluorine, chlorine, bromine or $C_1-C_4$-fluoroalkyl, for example trifluoromethyl, 2,2,2-trifluoroethyl or pentafluoroethyl.

Ar in formula (I) is very particularly preferably 2-thiophen-yl.

W in formula (I) is preferably COOR$^1$ where R$^1$ is hydrogen or $C_1-C_8$-alkyl.

R$^1$ in formula (I) is preferably $C_1-C_{12}$-alkyl, phenyl, o-, m- or p-tolyl, p-nitrophenyl or benzyl.

R$^1$ in formula (I) is particularly preferably methyl, ethyl, 2-ethoxyethyl, n-propyl, isopropyl, n-butyl, tert-butyl, n-pentyl, cyclohexyl and n-hexyl, and also trifluoromethyl, chloromethyl, benzyl and phenyl, and also 1,5-pentylene, 1,4-butylene and 1,3-propylene.

Very particularly preferred compounds of the formula (I) are
methyl 4-oxo-4-(phenyl)butanoate, methyl 4-oxo-4-[(2-, 3- or 4-methyl-; 2-, 3- or 4-ethyl-, 2-, 3- or 4-isopropyl; 2-, 3- or 4-tert-butyl-; 2-, 3- or 4-methoxy; 2-, 3- or 4-trifluoromethyl; 2-, 3- or 4-trifluoromethoxy-; 2-, 3- or 4-bromo-; 2-, 3- or 4-chloro-; 2-, 3- or 4-fluoro-; 2-, 3- or 4-cyano-; 2-, 3- or 4-methoxycarbonyl-; 2-, 3- or 4-dimethylamino-; 2-, 3- or 4-diethylamino-; 2-, 3- or 4-dimethylamino-; 2-, 3- or 4-methylamino)phenyl]butanoate, ethyl 4-oxo-4-(phenyl)butanoate, ethyl 4-oxo-4-[(2-, 3- or 4-methyl-; 2-, 3- or 4-ethyl-, 2-, 3- or 4-isopropyl; 2-, 3- or 4-tert-butyl-; 2-, 3- or 4-methoxy; 2-, 3- or 4-trifluoromethyl; 2-, 3- or 4-trifluoromethoxy-; 2-, 3- or 4-bromo-; 2-3- or 4-chloro-; 2-, 3- or 4-fluoro-; 2-, 3- or 4-cyano-; 2-, 3- or 4-methoxycarbonyl-; 2-, 3- or 4-dimethylamino-; 2-, 3- or 4-diethylamino-; 2-, 3- or 4-dimethylamino-; 2-, 3- or 4-methylamino)phenyl]butanoate, isopropyl 4-oxo-4-(phenyl)butanoate, isopropyl 4-oxo-4-[(2-, 3- or 4-methyl-; 2-, 3- or 4-ethyl-, 2-, 3- or 4-isopropyl; 2-, 3- or 4-tert-butyl-; 2-, 3- or 4-methoxy; 2-, 3- or 4-trifluoromethyl; 2-, 3- or 4-trifluoromethoxy-; 2-, 3- or 4-bromo-; 2-, 3- or 4-chloro-; 2-, 3- or 4-fluoro-; 2-, 3- or 4-cyano-; 2-, 3- or 4-methoxycarbonyl-; 2-, 3- or 4-dimethylamino-; 2-, 3- or 4-diethylamino-; 2-, 3- or 4-dimethylamino-; 2-, 3- or 4-methylamino)phenyl]butanoate, tert-butyl 4-oxo-4-(phenyl)butanoate, tert-butyl 4-oxo-4-[(2-, 3- or 4-methyl-; 2-, 3- or 4-ethyl-, 2-, 3- or 4-isopropyl; 2-, 3- or 4-tert-butyl-; 2-, 3- or 4-methoxy; 2-, 3- or 4-trifluoromethyl; 2-, 3- or 4-trifluoromethoxy-; 2-, 3- or 4-bromo-; 2-, 3- or 4-chloro-; 2-, 3- or 4-fluoro-; 2-, 3- or 4-cyano-; 2-, 3- or 4-methoxycarbonyl-; 2-, 3- or 4-dimethylamino-; 2-, 3- or 4-diethylamino-; 2-, 3- or 4-dimethylamino-; 2-, 3- or 4-methylamino)phenyl]butanoate, 2-ethylhexyl 4-oxo-4-(phenyl)butanoate, 2-ethylhexyl 4-oxo-4-[(2-, 3- or 4-methyl-; 2-, 3- or 4-ethyl-, 2-, 3- or 4-isopropyl; 2-, 3- or 4-tert-butyl-; 2-, 3- or 4-methoxy; 2-, 3- or 4-trifluoromethyl; 2-, 3- or 4-trifluoromethoxy-; 2-, 3- or 4-bromo-; 2-, 3- or 4-chloro-; 2-, 3- or 4-fluoro-; 2-, 3- or 4-cyano-; 2-, 3- or 4-methoxycarbonyl-; 2-, 3- or 4-dimethylamino-; 2-, 3- or 4-diethylamino-; 2-, 3- or 4-dimethylamino-; 2-, 3- or 4-methylamino)phenyl]butanoate, methyl 4-oxo-4-(2- or 3-thiophenyl-; 2- or 3-furanyl-; 2- or 3-pyrrolyl-; 3- or 4-pyrazolyl-; 1-, 2- or 4-thiazolyl-; 1-, 2- or 4-oxazolyl-; 2-, 4- or 5-imidazolyl-; 2-, 3- or 4-pyridyl-; 2- or 3-pyrazinyl-; 2-, 4- or 5-pyrimidyl; 3-, 4-, 5- or 6-pyridazinyl-; 2- or 3-indolyl-; 3-indazolyl-; indazolyl-; 2- or 3-benzofuranyl-; 2- or 3-benzothiophen-yl-; 2-, 3- or 4-quinolinyl- or isoquinolinyl)butanoate, ethyl 4-oxo-4-(2- or 3-thiophenyl-; 2- or 3-furanyl-; 2- or 3-pyrrolyl-; 3- or 4-pyrazolyl-; 1-, 2- or 4-thiazolyl-; 1-, 2- or 4-oxazolyl-; 2-, 4- or 5-imidazolyl-; 2-, 3- or 4-pyridyl-; 2- or 3-pyrazinyl-; 2-, 4- or 5-pyrimidyl; 3-, 4-, 5- or 6-pyridazinyl-; 2- or 3-indolyl-; 3-indazolyl-; indazolyl-; 2- or 3-benzofuranyl-; 2- or 3-benzothiophen-yl-; 2-, 3- or 4-quinolinyl- or isoquinolinyl)-butanoate, isopropyl-4-oxo-4-(2- or 3-thiophenyl-; 2- or 3-furanyl-; 2- or 3-pyrrolyl-; 3- or 4-pyrazolyl-; 1-, 2- or 4-thiazolyl-; 1-, 2- or 4-oxazolyl-; 2-, 4- or 5-imidazolyl-; 2-, 3- or 4-pyridyl-; 2- or 3-pyrazinyl-; 2-, 4- or 5-pyrimidyl; 3-, 4-, 5- or 6-pyridazinyl-; 2- or 3-indolyl-; 3-indazolyl-; indazolyl-; 2- or 3-benzofuranyl-; 2- or 3-benzothiophen-yl-; 2-, 3- or 4-quinolinyl- or isoquinolinyl)butanoate, tert-butyl 4-oxo-4-(2- or 3-thiophenyl-; 2- or 3-furanyl-; 2- or 3-pyrrolyl-; 3- or 4-pyrazolyl-; 1-, 2- or 4-thiazolyl-; 1-, 2- or 4-oxazolyl-; 2-, 4- or 5-imidazolyl-; 2-, 3- or 4-pyridyl-; 2- or 3-pyrazinyl-; 2-, 4- or 5-pyrimidyl; 3-, 4-, 5- or 6-pyridazinyl-; 2- or 3-indolyl-; 3-indazolyl-; indazolyl-; 2- or 3-benzofuranyl-; 2- or 3-benzothiophen-yl-; 2-, 3- or 4-quinolinyl- or isoquinolinyl)butanoate, 2-ethylhexyl 4-oxo-4-(2- or 3-thiophenyl-; 2- or 3-furanyl-; 2- or 3-pyrrolyl-; 3- or 4-pyrazolyl-; 1-, 2- or 4-thiazolyl-; 1-, 2- or 4-oxazolyl-; 2-, 4- or 5-imidazolyl-; 2-, 3- or 4-pyridyl-; 2- or 3-pyrazinyl-; 2-, 4- or 5-pyrimidyl; 3-, 4-, 5- or 6-pyridazinyl-; 2- or 3-indolyl-; 3-indazolyl-; indazolyl-; 2- or 3-benzofuranyl-; 2- or 3-benzothiophen-yl-; 2-, 3- or 4-quinolinyl- or isoquinolinyl)butanoate, and even greater preference is given to methyl 4-oxo-4-(2-thiophen-yl)-butanoate and ethyl 4-oxo-4-(2-thiophen-yl)-butanoate.

The process according to the invention is carried out in the presence of a ruthenium-containing catalyst.

For example and with preference, the catalysts used are those which comprise ruthenium complexes. Preferred ruthenium complexes are those which are obtainable by reacting compounds of the formula (II) with compounds of the formula (III), or complexes of the formula (IV). Particular preference is given to using those ruthenium complexes which are obtainable by reacting compounds of the formula (II) with compounds of the formula (III). In a preferred embodiment, the molar ratio of compounds of the formula (III) to compounds of the formula (If) is 2:1 to 3:1, particularly preferably 2.01:1 to 2.4:1.

Advantageously, compounds of the formula (III) and compounds of the formula (II) are mixed and the mixture is taken up in organic solvent. Before being added to the reaction mixture, the resulting mixture may also advantageously be admixed with a base, preferably an amine and stirred, for example and with preference, for 10 to 30 min, the molar amount of amine being, for example and with preference, 1:1 to 3:1, particularly preferably 1:1 to 2:1, based on compounds of the formula (III).

For organic solvents and amines, the same statements and preferred ranges apply as will be described in detail below.

In the compounds of the formula (II)

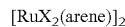  (II)

arene is a coordinated aromatic compound which has 6 to 12 ring carbon atoms and may also be substituted by up to 6 radicals which are each independently selected from the group of $C_1$-$C_8$-alkyl, benzyl and phenyl, and X is, for example and with preference, chlorine, bromine or iodine, more preferably chlorine.

Arene is preferably benzene or naphthalene which may be substituted by up to 6 radicals, each of which is selected independently from the group of methyl, ethyl, n-propyl, isopropyl and tert-butyl, Arene is preferably mesitylene, cumene or benzene.

Particularly preferred compounds of the formula (II) are (benzene)dichlororuthenium dimer, (mesitylene)dichlororuthenium dimer and (cumene)dichlororuthenium dimer, and even greater preference is given to (cumene)dichlororuthenium dimer.

In the formula (III)

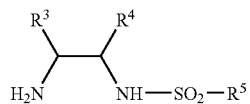  (III)

$R^3$ and $R^4$ are each independently, for example, $C_1$-$C_{20}$-alkyl, $C_4$-$C_{15}$-aryl or $C_5$-$C_{16}$-arylalkyl, or $R^3$ and $R^4$ together are a straight-chain or branched $C_3$-$C_{12}$-alkylene radical, and $R^5$ is $C_1$-$C_{20}$-alkyl, $C_1$-$C_{20}$-fluoroalkyl or $C_4$-$C_{15}$-aryl.

$R^3$ and $R^4$ are preferably identical and are each phenyl or are together straight-chain $C_3$-$C_8$-alkylene, for example 1,3-pentylene or 1,4-butylene, and $R^3$ and $R^4$ are particularly preferably identical and are each phenyl.

$R^5$ is preferably $C_1$-$C_4$-alkyl, $C_1$-$C_4$-fluoroalkyl, phenyl or naphthyl which may be substituted by no, one, two, three, four or five radicals which are selected from the group of $C_1$-$C_4$-alkyl, $C_1$-$C_4$-alkoxy, $C_1$-$C_4$-fluoroalkyl, fluorine and chlorine.

$R^5$ is particularly preferably methyl, trifluoromethyl, pentafluoroethyl, nona-fluorobutyl, phenyl, p-tolyl, p-ethylphenyl, p-anisyl, p-ethoxyphenyl, p-chlorophenyl, 2,4,6-trimethylphenyl, 2,4,6-triisopropylphenyl, p-fluorophenyl, pentafluorophenyl and naphthyl.

$R^5$ is particularly preferably p-tolyl, phenyl and naphthyl.

$R^5$ is very particularly preferably p-tolyl.

The compounds of the formula (M) preferably had a stereoisomeric purity of 90% or more, particularly preferably of 95% or more and very particularly preferably of 98.5% or more.

Compounds of the formula (III) include:

N-[(1R,2R) and (1S,2S)-2-amino-1,2-diphenylethyl]-p-tolylsulphonamide, N-[(1R,2R) and (1S,2S)-2-amino-1,2-diphenylethyl]-o-tolylsulphonamide, N-[(1R,2R) and (1S,2S)-2-amino-1,2-diphenylethyl]-m-tolylsulphonamide, N-[(1R,2R) and (1S,2S)-2-amino-1,2-diphenylethyl]phenylsulphonamide, N-[(1R,2R) and (1S,2S)-2-amino-1,2-diphenylethyl]-4-ethylphenylsulphonamide, N-[(1R,2R) and (1S,2S)-2-amino-1,2-diphenylethyl]-3-ethylphenylsulphonamide, N-[(1R,2R) and (1S,2S)-2-amino-1,2-diphenylethyl]-2-ethylphenylsulphonamide, N-[(1R,2R) and (1S,2S)-2-amino-1,2-diphenylethyl]-2,4,6-trimethylphenylsulphonamide, N-[(1R,2R) and (1S,2S)-2-amino-1,2-diphenylethyl]-2,4,6-triisopropylphenylsulphonamide, N-[(1R,2R) and (1S,2S)-2-amino-1,2-diphenylethyl]-4-chlorophenylsulphonamide, N-[(1R,2R) and (1S,2S)-2-amino-1,2-diphenylethyl]-3-chlorophenylsulphonamide, N-[(1R,2R) and (1S,2S)-2-amino-1,2-diphenylethyl]-2-chlorophenylsulphonamide, N-[(1R,2R) and (1S,2S)-2-amino-1,2-diphenylethyl]-4-fluorophenylsulphonamide, N-[(1R,2R) and (1S,2S)-2-amino-1,2-diphenylethyl]-3-fluorophenylsulphonamide, N-[(1R,2R) and (1S,2S)-2-amino-1,2-diphenylethyl]-2-fluorophenylsulphonamide, N-[(1R,2R) and (1S,2S)-2-amino-1,2-diphenylethyl]-4-methoxyphenylsulphonamide, N-[(1R,2R) and (1S,2S)-2-amino-1,2-diphenylethyl]-3-methoxyphenylsulphonamide, N-[(1R,2R) and (1S,2S)-2-amino-1,2-diphenylethyl]-2-methoxyphenylsulphonamide, N-[(1R,2R) and (1S,2S)-2-amino-1,2-diphenylethyl]-1-naphthylsulphonamide, N-[α(1R,2R) and (1S,2S)-2-amino-1,2-diphenylethyl]-2-naphthylsulphonamide, N-[(1R,2R) and (1S,2S)-2-amino-1,2-diphenylethyl]pentafluorophenylsulphonamide, N-[(1R,2R) and (1S,2S)-2-amino-1,2-diphenylethyl]methanesulphonamide, N-[(1R,2R) and (1S,2S)-2-amino-1,2-diphenylethyl]trifluoromethanesulphonamide, N-[(1R,2R) and (1S,2S)-2-aminocyclohexyl]-p-tolylsulphonamide, N-[(1R,2R) and (1S,2S)-2-aminocyclohexyl]-O-tolylsulphonamide, N-[(1R,2R) and (1S,2S)-2-aminocyclohexyl]-m-tolylsulphonamide, N-[(1R,2R) and (1S,2S)-2-aminocyclohexyl]-phenylsulphonamide, N-[(1R,2R) and (1S,2S)-2-aminocyclohexyl]-4-ethylphenylsulphonamide, N-[(1R,2R) and (1S,2S)-2-aminocyclohexyl]-3-ethylphenylsulphonamide, N-[(1R,2R) and (1S,2S)-2-aminocyclohexyl]-2-ethylphenylsulphonamide, N-[(1R,2R) and (1S,2S)-2-aminocyclohexyl]-2,4,6-trimethylphenylsulphonamide, N-[(1R,2R) and (1S,2S)-2-aminocyclohexyl]-2,4,6-triisopropylphenylsulphonamide, N-[(1R,2R) and (1S,2S)-2-aminocyclohexyl]-4-chlorophenylsulphonamide, N-[(1R,2R) and (1S,2S)-2-aminocyclohexyl]-3-chlorophenylsulphonamide, N-[(1R,2R) and (1S,2S)-2-aminocyclohexyl]-2-chlorophenylsulphonamide, N-[(1R,2R) and (1S,2S)-2-aminocyclohexyl]-4-fluorophenylsulphonamide, N-[(1R,2R) and (1S,2S)-2-aminocyclohexyl]-3-fluorophenylsulphonamide, N-[(1R,2R) and (1S,2S)-2-aminocyclohexyl]-2-fluorophenylsulphonamide, N-[(1R,2R) and (1S,2S)-2-aminocyclohexyl]-4-methoxyphenylsulphonamide, N-[(1R,2R) and (1S,2S)-2-aminocyclohexyl]-3-methoxyphenylsulphonamide, N-[(1R,2R) and (1S,2S)-2-aminocyclohexyl]-2-methoxyphenylsulphonamide, N-[(1R,2R) and (1S,2S)-2-amino-cyclohexyl]-1-naphthylsulphonamide, N-[(1R,2R) and (1S,2S)-2-aminocyclohexyl]-2-naphthylsulphonamide, N-[(1R,2R) and (1S,2S)-2-aminocyclohexyl]-pentafluoro-phenylsulphonamide, N-[(1R,2R) and (1S,2S)-2=aminocyclohexyl]-methane-sulphonamide, N-[(1R,2R) and (1S,2S)-2-aminocyclohexyl]-trifluoromethanesulphonamide, N-[(1R,2R) and (1S,2S)-2-aminocyclopentyl]-p-tolylsulphonamide, N-[(1R,2R) and (1S,2S)-2-aminocyclopentyl]-o-tolylsulphonamide, N-[(1R,2R) and (1S,2S)-2-aminocyclopentyl]-m-tolylsulphonamide, N-[(1R,2R) and (1S,2S)-2-aminocyclopentyl]-phenylsulphonamide, N-[(1R,2R) and (1S,2S)-2-aminocyclopentyl]-4-ethylphenyl-sulphonamide, N-[(1R,2R) and (1S,2S)-2-aminocyclopentyl]-3-ethylphenylsulphonamide, N-[(1R,2R) and (1S,2S)-2-aminocyclopentyl]-2-ethylphenylsulphonamide, N-[(1R,2R) and (1S,2S)-2-aminocyclopentyl]-2,4,6-trimethylphenylsulphonamide, N-[(1R,2R) and (1S,2S)-2-aminocyclopentyl]-2,4,6-triisopropylphenylsulphonamide, N-[(1R,2R) and (1S,2S)-2-aminocyclopentyl]-4-chlorophenylsulphonamide, N-[(1R,2R) and (1S,2S)-2-aminocyclopentyl]-3-chlorophenylsulphonamide, N-[(1R,2R) and (1S,2S)-2-aminocyclopentyl]-2-chlorophenylsulphonamide, N-[(1R,2R) and (1S,2S)-2-aminocyclopentyl]-4-fluorophenylsulphonamide, N-[(1R,2R) and (1S,2S)-2-aminocyclopentyl]-3-fluorophenylsulphonamide, N-[(1R,2R) and (1S,2S)-2-aminocyclopentyl]-2-fluorophenylsulphonamide, N-[(1R,2R) and (1S,2S)-2-aminocyclopentyl]-4-methoxyphenylsulphonamide, N-[(1R,2R) and (1S,2S)-2-aminocyclopentyl]-3-methoxyphenylsulphonamide, N-[(1R,2R) and (1S,2S)-2-aminocyclopentyl]-2-methoxyphenylsulphonamide, N-[(1R,2R) and (1S,2S)-2-aminocyclopentyl]-1-naphthylsulphonamide, N-[(1R,2R) and (1S,2S)-2-aminocyclopentyl]-2-naphthylsulphonamide, N-[(1R,2R) and (1S,2S)-2-aminocyclopentyl]-pentafluorophenylsulphonamide, N-[(1R,2R) and (1S,2S)-2-aminocyclopentyl]-methanesulphonamide, N-[(1R,2R) and (1S,2S)-2-aminocyclopentyl]trifluoromethanesulphonamide.

In the formula (IV)

$$[RuX_2(arene)\{(III)\}] \quad (IV),$$

arene and X each have the definitions and preferred ranges given under formula (II) and (M) in the formula (IV) represents compounds of the formula (M) having the definitions and preferred ranges given there.

Compounds of the formula (IV) include:
[N-[(1R,2R and 1S,2S)-2-(amino-κN)-1,2-diphenylethyl]-p-tolylsulphonamidato-κN]chloro[($\eta^6$)-cumene]ruthenium(II), [N-[(1R,2R and 1S,2S)-2-(amino-κN)-1,2-diphenylethyl]phenylsulphonamidato-κN]chloro[($\eta^6$)-cumene]ruthenium(II), [N-[(1R,2R and 1S,2S)-2-(amino-κN)-1,2-diphenylethyl]-2,4,6-trimethylphenylsulphon-amidato-κN]chloro[($\eta^6$)-cumene]ruthenium(II), [N-[(1R,2R and 1S,2S)-2-(amino-κN)-1,2-diphenylethyl]-4-chlorophenylsulphonamidato-κN]chloro[($\eta^6$)-cumene]ruthenium(II), [N-[(1R,2R and 1S,2S)-2-(amino-κN)-1,2-diphenylethyl]-4-fluorophenylsulphonamidato-κN]chloro[($\eta^6$)-cumene]ruthenium(II) [N-[(1R,2R and 1S,2S)-2-(amino-κN)-1,2-diphenylethyl]-4-methoxyphenylsulphonamidato-κN]chloro[($\eta 6$)-cumene]ruthenium(II) [N-[(1R,2R and 1S,2S)-2-(amino-κN)-1,2-diphenylethyl]-1-naphthylsulphonamidato-κN]chloro[($\eta^6$)-cumene]ruthenium(II) [N-[(1R,2R and 1S,2S)-2-(amino-κN)-1,2-diphenylethyl]pentafluorophenylsulphonamidato-κN]chloro[($\eta^6$)-cumene]ruthenium(II) [N-[(1R,2R and 1S,2S)-2-(amino-κN)-1,2-diphenylethyl] methanesulphonamidato-κN]chloro[($\eta^6$)-cumene] ruthenium(II) [N-[(1R,2R and 1S,2S)-2-(amino-κN)-1,2-diphenylethyl]trifluoromethanesulphon-amidato-κN] chloro[($\kappa^6$)-cumene]ruthenium(II) [N-[(1R,2R and 1S,2S)-2-(amino-κN)-1,2-diphenylethyl]-p-tolylsulphonamidato-κN]chloro[($\eta^6$)-1,3,5-trimethylbenzene]ruthenium(II) [N-[(1R,2R and 1S,2S)-2-(amino-κN)-1,2-diphenylethyl]-p-tolylsulphonamidato-κN]chloro [($\eta^6$)-benzene]ruthenium(II) [N-[(1R,2R and 1S,2S)-2-(amino-κN)-1,2-diphenylethyl]-2,4,6-trimethylphenylsulphonamidato-κN]chloro[($\eta^6$)-benzene]ruthenium(II) [N-[(1R,2R and 1S,2S)-2-(amino-κN)-1,2-diphenylethyl]-1-naphthylsulphonamidato-κN]chloro[($\eta^6$)-benzene] ruthenium(II) [N-[(1R,2R and 1S,2S)-2-(amino-κN)-1,2-diphenylethyl]pentafluorophenylsulphonamidato-κN] chloro[($\eta^6$)-benzene]ruthenium(II) [N-[(1R,2R and 1S,2S)-2-(amino-κN)-cyclohexyl]-p-tolylsulphonamidato-κN]chloro[($\eta^6$)-cumene]ruthenium(II) [N-[(1R,2R and 1S,2S)-2-(amino-κN)-cyclohexyl]phenylsulphonamidato-κN]chloro[($\eta^6$)-cumene]ruthenium(II) [N-[(1R,2R and 1S,2S)-2-(amino-κN)-cyclohexyl]-2,4,6-trimethylphenylsulphonamidato-κN]chloro[($\eta^6$)-cumene]ruthenium(II) [N-[(1R,2R and 1S,2S)-2-(amino-κN)-cyclohexyl]-4-chlorophenylsulphonamidato-κN]chloro[($\eta^6$)-cumene]ruthenium(II) [N-[(1R,2R and 1S,2S)-2-(amino-κN)-cyclohexyl]-4-luorophenylsulphonamidato-κN] chloro[($\eta^6$)-cumene]ruthenium(II) [N-[(1R,2R and 1S,2S)-2-(amino-κN)-cyclohexyl]-4-methoxyphenylsulphonamidato-κN]chloro[($\eta^6$)-cumene]ruthenium(II) [N-[(1R,2R and 1S,2S)-2-(amino-κN)-cyclohexyl]-1-naphthylsulphonamidato-κN]chloro [($\eta^6$)-cumene]ruthenium(II) [N-[(1R,2R and 1S,2S)-2-(amino-κN)-cyclohexyl]methanesulphonamidato-κN)]chloro[($\eta^6$)-cumene] ruthenium(II) [N-[(1R,2R and 1S,2S)-2-(amino-κN)-cyclohexyl]trifluoromethanesulphonamidato-κN]chloro [($\eta^6$)-cumene]ruthenium(II) [N-[(1R,2R and 1S,2S)-2-(amino-κN)-cyclohexyl]-p-tolylsulphonamidato-κN] chloro[($\eta^6$)-benzene]ruthenium(II) [N-[(1R,2R and 1S,2S)-2-(amino-κN)-cyclohexyl]-2,4,6-trimethylphenylsulphonamidato-κN]chloro[($\eta^6$)-benzene]ruthenium (II) [N-[(1R,2R and 1S,2S)-2-(amino-κN)-cyclohexyl]-p-tolylsulphonamidato-κN]chloro[($\eta^6$)-1,3,5-trimethylbenzene]ruthenium(II)

Particularly preferred catalysts for the purposes of the invention are those which comprise ruthenium complexes which are obtainable by reacting S,S— or R,R—N-p-toluene-sulphonyl-1,2-diphenylethylenediamine with (cumene) dichlororuthenium dimer.

The process according to the invention is carried out in the presence of at least one amine, preferably an amine of which at least some is present in protonated form.

Also, formic acid, formates or mixtures thereof are used for the process according to the invention.

Preference is giving to using mixtures of formic acid with amines. In this way, the corresponding ammonium formates are at least partially formed and can be used in a similar manner.

Useful amines are in particular those of the formula (V)

$$NR^6R^7R^8 \quad (V)$$

where
$R^6$, $R^7$ and $R^8$ are each independently hydrogen, $C_1$-$C_8$-alkyl or benzyl.

Particularly preferred amines are ammonia and those of the formula (V) where $R^6$, $R^7$ and $R^8$ are each independently $C_1$-$C_8$-alkyl or benzyl.

Particularly preferred amines are those of the formula (V) where $R^6$, $R^7$ and $R^8$ are identical and are each ethyl, n-butyl or n-hexyl, and even greater preference is given to the use of triethylamine.

The molar ratio of formic acid to amine may be, for example, 1:1 to 3:1, and preference is given to a ratio of 1.01:1 to 1.5:1.

The molar ratio of formic acid based on substrate used may be, for example, 1:1 to 3:1, and preference is given to 1:1 to 1.5:1, particular preference to 1.02:1 to 1.1:1.

The process according to the invention may be carried out in the presence or absence, preferably in the presence, of organic solvent.

Examples of suitable organic solvents include:
amides, for example dimethylformamide, N-methylpyrrolidinone, optionally halogenated aliphatic or aralphatic solvents having up to 16 carbon atoms, for example toluene, o-, m- and p-xylene, chloroform, dichloromethane, chlorobenzene, the isomeric dichlorobenzenes, fluorobenzene, nitriles, for example acetonitrile, benzonitrile, dimethyl sulphoxide or mixtures thereof.

Preferred solvents are acetonitrile, N-methylpyrrolidinone, chloroform, dichloromethane, chlorobenzene, the isomeric dichlorobenzenes, fluorobenzene or mixtures thereof, and particular preference is given to dichloromethane, acetonitrile, N-methylpyrrolidone or mixtures thereof.

The reaction temperature may be, for example, $-10$ to $150°$ C., and preference is given to 20 to $100°$ C., particular preference to 20 to $80°$ C.

The reaction times are, for example, between 0.5 h to 48 h, preferably between 6 and 24 h.

The molar amount of ruthenium may be, for example, 0.01 to 1.0 mol %, based on the substrate used, and preference is given to 0.02 to 0.2 mol %, very particular preference to 0.02 to 0.1 mol %.

It is advantageous, although not obligatory, to carry out the reaction in a substantially oxygen-free atmosphere. Substantially oxygen-free means, for example, a content of 0 to 1% by volume, preferably 0 to 0.1% by volume, of oxygen.

The reaction may be accelerated by removing carbon dioxide which is released during the reaction. Advantageous, and therefore encompassed by the invention, is intensive stirring of the reaction mixture at an average stirrer speed of, for example, 100 to 3000 min$^{-1}$, preferably 500 to 1500 min$^{-1}$. Alternatively, or in supplementation thereto, the removal of carbon dioxide may be supported by passing an inert gas stream through or over the reaction mixture. Examples of suitable gases include nitrogen, noble gases, for example argon, or mixtures thereof.

In the manner according to the invention, stereoisomerically enriched 4-aryl-4-hydroxybutanoic acid derivatives of the formula (VI)

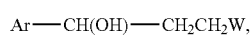

where Ar and W have the same definitions and preferred ranges as were named under the formula (I) are obtained.

Depending on the choice of the configuration of the ligands, the S- or R-configured products at the 4-position are obtainable.

A particularly preferred embodiment of the process according to the invention is described hereinbelow, without imposing any limitation.

In a stirred tank, a 1:1 mixture (molar) of formic acid and triethylamine is prepared by simple mixing and the 4-aryl-4-ketobutanoic acid derivative is added to this biphasic mixture equimolar or in a slight deficiency. Depending on the solubility of the substrate, an amount of an organic solvent is added. This mixture is inertized by passing through nitrogen and the mixture is heated to the desired reaction temperature with vigorous stirring.

The catalyst is added to this mixture as a solution in dichloromethane in molar ratios compared to the substrate of, for example, 1:500 to 1:5000, and the reaction mixture is stirred for the desired time. The conversion is followed by chromatography.

The reaction mixture may subsequently be worked up by processes known to those skilled in the art. It has proven advantageous to add solvents and dilute aqueous hydrochloric acid or water to the reaction mixture for workup. After phase separation, the product may be isolated in a manner known per se from the organic phase either distillatively or by a suitable crystallization process.

The 4-aryl-4-hydroxybutanoic acid derivatives which can be prepared according to the invention are suitable in particular for use in a process for preparing liquid-crystalline compounds, agrochemicals and pharmaceuticals or intermediates thereof.

Preferred pharmaceuticals are serotonin take-up inhibitors, for example fluoxetin and duloxetin.

In particular, the 4-aryl-4-hydroxybutanoic acid derivatives which can be prepared according to the invention are suitable for preparing compounds of the formulae (VII), (VII), (IX) and (X),

where, in each case,
Ar is as defined in formula (I) and,
in the formulae (VIII), (IX) and (X), $R^1$ is as defined in formula (I) and n=two.

The compounds of the formula (VII) may be prepared, for example, by base-catalyzed cyclization of compounds of the formula (VI) where W is COOR$^1$, as defined there. When compounds of the formula (VI) where W is COOR$^1$ as defined there are used, some of the compounds of the formula (VII) may also be are observed as a reaction product of the process according to the invention, in a proportion of up to 20%, although typically up to 10 mol %, based on the hydroxy ester obtainable as the main product.

The compounds of the formula (IX) may be prepared, for example, by converting compounds of the formula (VI) to compounds of the formula (VII) by amination, if appropriate, and converting the compounds of the formula (VII) to compounds of the formula (IX) by oxidation with hypochlorite.

The compounds of the formula (X) may be prepared, for example, by reducing compounds of the formula (VIII) in a manner known per se using complex hydrides, for example lithium aluminium hydride.

The advantage of the present invention is that 4-aryl-4-hydroxybutanoic acid derivatives can be obtained in stereoisomerically enriched form in a manner which is efficient and can be performed in a technically simple manner to achieve high catalyst turnover numbers.

EXAMPLES

General Procedure for the Transfer Hydrogenation of 4-aryl-4-oxobutanoic Acid Derivatives Examples 1-11

In a Schlenk vessel, the catalyst solution is prepared by weighing in 2.03 molar equivalents of 1S,2S—N-(p-toluenesulphonyl)-1,2-diphenylethylenediamine (S,S-TsDPEN) and 1 molar equivalent of [(cumene)RuCl$_2$]$_2$, stirring this mixture in 5 ml of dichloromethane and admixing with 2 molar equivalents of triethylamine.

In a multi-necked flask equipped with a sparging stirrer, reflux condenser and thermometer, a formic acid/triethylamine mixture (molar ratio 1:1, molar ratio 1.05:1 based on the substrate) is prepared by slowly adding formic acid dropwise to triethylamine via a dropping funnel within 5 min with stirring and ice-cooling. The appropriate keto compound is then added to this biphasic mixture (100-5000 eq. based on the catalyst), the homogeneous yellow solution is optionally admixed with solvent, and the entire mixture is degassed by passing through argon for 20 min. It is heated to the target temperature and the dark red catalyst solution is added all at once by syringe to the reaction mixture with vigorous stirring. The mixture is stirred under argon for the stated time.

The mixture is diluted with water and dichloromethane and stirred for a further 10 min, and, after phase separation, the aqueous phase is extracted twice with dichloromethane. The combined organic phases are washed with NaCl solution, dried over MgSO$_4$ and filtered, and then the solvent is removed on a rotary evaporator. The crude product is either distilled and recrystallized, for example from hexane/petroleum ether or from hexane/dichloromethane, or used as a crude mixture in further reactions. A mixture is usually obtained of hydroxy esters and lactones in ratios of 99:1 to 80:20 in favour of the hydroxyester. The complete conversion to the corresponding lactones (see formula VII) is effected by stirring the mixture with 2 N NaOH solution at 60° C. for 1 h.

The conversion and enantiomer analysis was effected by gas chromatography using IVA capillary columns. IVADEX 1 (column A), IVADEX 3 (column B), and hydrodex-β-6-TBDM (column C) columns of length 12-25 m were used, using helium as the carrier gas on an HP 5890 II gas chromatograph. The conversions and reaction times reported here are not optimized, since operation was usually effected in closed vessels without removal of CO$_2$.

Ethyl 4-hydroxy-4-phenylbutanoate (1)

$^1$H NMR (d$^1$-chloroform, 400 MHz): δ=7.3-7.1 (m, 5H, Ph), 5.45 (pt, 1H, CHOH), 4.07 (q, 2H, OCH2), 2.36 (t, 2H, CH2), 2.01 (m, 3H, $\overline{CH2}$ and OH), 1.18 (t, 3H, CH3) ppm.
ee: 92.0%, t=66 h, C=71.5%. S/C=400, T=30° C.
Chiral GC: 12.39, 12.92 min (column C, 20 m, 160° C. isothermal).

Ethyl 4-hydroxy-4-phenylbutanoate (2)

t=24 h, C=62%. S/C=400, T=30° C.

Methyl 4-hydroxy-4-(4-bromophenyl)butanoate (3)

$^1$H NMR (d$^1$-chloroform, 400 MHz): δ=7.45 (d, 2H, Ph), 7.14 (d, 2H, Ph), 5.40 (pt, 1H, CHOH), 3.42 (s, 3H, CH3), 2.37 (t, 2H, CH2), 2.20 (br, 1H, $\overline{OH}$), 1.98 (pq, 2H, CH2) ppm.
ee: 89.9%, t=66 h, C=96%. S/C=400, T=30° C.
Chiral GC: ester: 18.98, 19.64 min, lactone: 16.20, 17.24 min (column A, 12.5 m, 15 min 160° C., 2° C./min, 220° C.).

Methyl 4-hydroxy-4-(4-bromophenyl)butanoate (4)

t=24 h, C=95%. S/C=100, T=30° C.

Methyl 4-hydroxy-4-(4-methoxyphenyl)butanoate (5)

ee: 91.8%, S/C=400, T=30° C.
Chiral GC: lactone: 20.08, 20.41 min (Column A, 12.5 m, 15 min 145° C., 5° C./min, 180° C.).

Ethyl 4-hydroxy-4-(2-thienyl)butanoate (6)

$^1$H NMR (d$^1$-chloroform, 400 MHz): δ=7.17 (d, 1H, Ar), 6.89 (m, 3H, Ar), 4.95 (pt, 1H, CHOH), 4.09 (q, 2H, OCH2), 2.40 (m, 3H, CH2 and OH), 2.01 (pq, 2H, CH2), 1.19 (t, 3H, CH3) ppm.
ee: 96.00%, S/C=500, C=98%, t=60 h, T=0.30° C.
Chiral GC: hydroxy ester: 13.30, 13.63; lactone, 6.77, 7.04 min. (Column A, 12.5 m, 15 min 145° C., 5° C./min, 180° C.).

Ethyl 4-hydroxy-4-(2-thienyl)butanoate (7)

ee: 94.8%, S/C=100, C=91.7%, t=18 h, T 30° C.

Methyl 4-hydroxy-4-(2,4-dichlorothien-3-yl)butanoate (8)

$^1$H NMR (d$^1$-chloroform, 400 MHz): δ=6.82 (s, 1H, Ar), 4.81 (dd, 1H, CHOH), 3.62 (s, 3H, CH3), 2.39 (t, 2H, CH2), 2.20 (br, 3H, O$\overline{H}$ and CH2) ppm.
ee: 70.00%, S/C=200, U=36.5%, t=66 h, T=30° C.
Chiral GC: hydroxy ester: 21.62, 22.08; lactone; 18.02, 18.44 min. (Column A, 12.5 m, 15 min 145° C., 5° C./min, 180° C.).

Methyl 4-hydroxy-4-(2,4-dichlorothien-3-yl)butanoate (9)

S/C=100, C=97%, t=24 h, T=30° C.

Ethyl 4-hydroxy-4-(2-thienyl)butanoate (10)

The conversion was effected in a similar manner to Example 6, except that 0.004 eq. of [N-[(1R,2R and 1S,2S)-2-(amino-κN)-1,2-diphenylethyl]-p-tolylsulphonamidato-κN]chloro[(η$^6$)_1,3,5-trimethylbenzene]ruthenium(II) was used as catalyst.
ee: 94.8%, S/C=250, C=80%, t=26 h, T=30° C.

Ethyl 4-hydroxy-4-(2-thienyl)butanoate (11)

The conversion was effected in a similar manner to Example 6, except that 0.002 eq. of [N-[(1R,2R and 1S,2S)-

2-(amino-κN)-1,2-diphenylethyl]-p-tolylsulphonamidato-κN]chloro[(η⁶)-1,3,5-trimethylbenzene]ruthenium(II) was used as catalyst.

ee: 94.3%, S/C=500, C>98%, t=60 h, T=30° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing compounds of the formula (IX),

  (IX)

where, in each case,
aryl is as defined as phenyl having no or one radical selected from the group consisting of O—($C_1$-$C_{12}$-alkyl) and bromine, or 2-thiophenyl and 3-thiophnyl having no, one, or two radicals of chlorine and,
$R^1$ is in each case independently hydrogen, or $C_1$-$C_{20}$-alkyl, and
n=two comprising providing stereoisomerically enriched compounds of formula (VIII)

  (VIII)

wherein Aryl, $R^1$ and n are defined above,
prepared by a process comprising reacting
a) compounds of the formula (I)

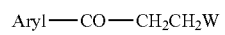  (I)

Where Aryl is defined as above,
W is C(O)Y$R^1_n$ where Y is oxygen and n=1 or Y is nitrogen and n=2, or
W is CN, and
$R^1$ is defined as above,
b) in the presence of a ruthenium-containing catalyst, and
c) in the presence of at least one amine which is present at least partly in protonated form,
d) with formic acid, formate or mixtures thereof,
and converting the compound of the formula (VIII) to compounds of formula (IX) by oxidation.

* * * * *